(12) United States Patent  
Scheidemann et al.

(10) Patent No.: US 7,550,722 B2
(45) Date of Patent: Jun. 23, 2009

(54) FOCAL PLANE DETECTOR ASSEMBLY OF A MASS SPECTROMETER

(75) Inventors: Adi A. Scheidemann, Baden (CH); Gottfried P. Kibelka, Birmingham, AL (US); Clare R. Long, Edmonds, WA (US); Mark W. Dassel, Indianola, WA (US)

(73) Assignee: OI Corporation, College Station, TX (US)

( * ) Notice: Subject to any disclaimer, the term of this patent is extended or adjusted under 35 U.S.C. 154(b) by 215 days.

(21) Appl. No.: 11/073,426

(22) Filed: Mar. 4, 2005

(65) Prior Publication Data

US 2006/0011826 A1      Jan. 19, 2006

Related U.S. Application Data

(60) Provisional application No. 60/557,920, filed on Mar. 31, 2004, provisional application No. 60/557,969, filed on Mar. 31, 2004, provisional application No. 60/550,663, filed on Mar. 5, 2004, provisional application No. 60/550,664, filed on Mar. 5, 2004.

(51) Int. Cl.
*H01J 49/32* (2006.01)
(52) U.S. Cl. .................. 250/299; 250/281; 250/309
(58) Field of Classification Search .................. 250/299
See application file for complete search history.

(56) References Cited

U.S. PATENT DOCUMENTS 2,309,414 A    1/1943  Nobbs ..................... 171/264
2,964,627 A    12/1960 Wild ....................... 250/41.9
3,478,204 A    11/1969 Brubaker et al. ........... 250/41.9
3,521,054 A    7/1970  Webb ...................... 250/41.9
3,555,331 A    1/1971  Chuan ..................... 313/7
3,898,456 A    8/1975  Dietz ...................... 250/299

(Continued)

FOREIGN PATENT DOCUMENTS

EP          0 745 847 A2    12/1996

(Continued)

OTHER PUBLICATIONS

Birkinshaw, Keith, "Fundamentals of Focal Plane Detectors," *Journal of Mass Spectrometry*, 32 795-806, 1997.

(Continued)

*Primary Examiner*—David A. Vanore
*Assistant Examiner*—Phillip A. Johnston
(74) *Attorney, Agent, or Firm*—Seed IP Law Group PLLC (57) ABSTRACT

A focal plane detector assembly of a mass spectrometer includes an ion detector configured to detect ions crossing a focal plane of the spectrometer and an electrically conductive mesh lying in a plane parallel to the focal plane, positioned such that ions exiting a magnet of the mass spectrometer pass through the mesh before contacting the ion detector. The mesh is maintained at a low voltage potential, relative to a circuit ground, which shields ions passing through the magnet from high voltage charges from other devices, such as microchannel plate electron multipliers. The mesh may be mounted directly to the magnet or positioned some distance away. The detector array may include any suitable device, including a faraday cup detector array, a strip charge detector array, or a CCD detector array.

30 Claims, 5 Drawing Sheets

U.S. PATENT DOCUMENTS

| | | | | |
|---|---|---|---|---|
| 4,016,421 | A | 4/1977 | Hull et al. | 250/281 |
| 4,071,848 | A | 1/1978 | Leeper | 343/844 |
| 4,182,984 | A | 1/1980 | MacFadden et al. | 324/152 |
| 4,409,482 | A | 10/1983 | Scheid et al. | 250/282 |
| 4,456,898 | A | 6/1984 | Frischmann | 335/217 |
| 4,476,732 | A | 10/1984 | Yang | 73/863.73 |
| 4,672,204 | A | 6/1987 | Slodzian et al. | 250/298 |
| 4,757,198 | A | 7/1988 | Korte et al. | 250/288 |
| 4,808,818 | A * | 2/1989 | Jung | 250/282 |
| 4,855,747 | A | 8/1989 | Steinberg | 342/179 |
| 4,859,848 | A | 8/1989 | Bowman et al. | 250/296 |
| 4,988,867 | A | 1/1991 | Laprade | 250/281 |
| 5,038,149 | A | 8/1991 | Aubry et al. | 342/372 |
| 5,039,280 | A | 8/1991 | Saulgeot et al. | 417/205 |
| 5,046,018 | A | 9/1991 | Flewelling et al. | |
| 5,135,870 | A | 8/1992 | Williams et al. | 436/173 |
| 5,146,088 | A | 9/1992 | Kingham et al. | 250/288 |
| 5,231,591 | A | 7/1993 | Flewelling et al. | |
| 5,259,735 | A | 11/1993 | Takahashi et al. | 417/203 |
| 5,264,813 | A | 11/1993 | Byers, Jr. | 335/217 |
| 5,299,577 | A | 4/1994 | Brown et al. | 128/660.07 |
| 5,313,061 | A | 5/1994 | Drew et al. | 250/281 |
| 5,317,151 | A | 5/1994 | Sinha et al. | 250/298 |
| 5,331,158 | A | 7/1994 | Dowell | 250/287 |
| 5,382,793 | A | 1/1995 | Weinberger et al. | 250/288 |
| 5,386,115 | A | 1/1995 | Freidhoff et al. | 250/281 |
| 5,461,235 | A | 10/1995 | Cottrell et al. | 250/288 |
| 5,490,765 | A | 2/1996 | Bailey et al. | 417/2 |
| 5,561,292 | A * | 10/1996 | Buckley et al. | 250/288 |
| 5,686,655 | A | 11/1997 | Itoi | 73/23.37 |
| 5,801,380 | A * | 9/1998 | Sinha | 250/299 |
| 5,808,299 | A | 9/1998 | Syage | 250/288 |
| 5,929,819 | A | 7/1999 | Grinberg | 343/754 |
| 6,004,109 | A | 12/1999 | Gebele et al. | 417/243 |
| 6,046,451 | A | 4/2000 | Sinha | 250/298 |
| 6,051,831 | A | 4/2000 | Koster | 250/281 |
| 6,051,832 | A | 4/2000 | Bradshaw | 250/286 |
| 6,135,971 | A | 10/2000 | Hutchinson et al. | 601/3 |
| 6,155,097 | A | 12/2000 | Arnold | 73/23.35 |
| 6,180,942 | B1 | 1/2001 | Tracy et al. | 250/299 |
| 6,182,831 | B1 | 2/2001 | Scheidemann et al. | 209/213 |
| 6,191,419 | B1 | 2/2001 | Sinha | 250/294 |
| 6,195,705 | B1 | 2/2001 | Leung | 709/245 |
| 6,198,096 | B1 | 3/2001 | Le Cocq | 250/287 |
| 6,300,626 | B1 | 10/2001 | Brock et al. | 250/287 |
| 6,316,768 | B1 | 11/2001 | Rockwood et al. | 250/287 |
| 6,403,956 | B1 | 6/2002 | Sinha | 250/298 |
| 6,576,899 | B2 | 6/2003 | Sinha et al. | 250/299 |
| 6,614,019 | B2 * | 9/2003 | Feller et al. | 250/287 |
| 6,635,883 | B2 | 10/2003 | Torti et al. | 250/423 R |
| 6,646,256 | B2 | 11/2003 | Gourley et al. | 250/288 |
| 6,649,908 | B2 | 11/2003 | Apffel, Jr. et al. | 250/288 |
| 6,680,477 | B2 | 1/2004 | Beck et al. | 250/288 |
| 6,734,423 | B2 | 5/2004 | Bryden | 250/288 |
| 6,750,448 | B2 * | 6/2004 | Turecek et al. | 250/281 |
| 6,831,276 | B2 | 12/2004 | Berger et al. | |
| 6,838,663 | B2 | 1/2005 | Coon et al. | 250/288 |
| 6,839,476 | B2 | 1/2005 | Kim et al. | |
| 6,843,375 | B2 | 1/2005 | Scheidemann et al. | 209/213 |
| 6,847,036 | B1 | 1/2005 | Darling et al. | 250/291 |
| 6,858,839 | B1 | 2/2005 | Anderson et al. | 250/281 |
| 6,879,423 | B2 | 4/2005 | Kim et al. | |
| 6,906,333 | B2 | 6/2005 | Scheidemann et al. | 250/398 |
| 6,978,058 | B2 | 12/2005 | Kim et al. | |
| 6,979,818 | B2 | 12/2005 | Scheidemann et al. | 250/299 |
| 7,075,072 | B2 * | 7/2006 | Hatakeyama et al. | 250/310 |
| 7,197,202 | B2 | 3/2007 | Kim et al. | |
| 2002/0117617 | A1 | 8/2002 | Sinha et al. | 250/299 |
| 2003/0197121 | A1 * | 10/2003 | Turecek et al. | 250/281 |
| 2004/0109627 | A1 | 6/2004 | Kim et al. | |
| 2004/0109628 | A1 | 6/2004 | Kim et al. | |
| 2004/0120631 | A1 | 6/2004 | Kim et al. | |
| 2004/0136099 | A1 | 7/2004 | Kim et al. | |
| 2004/0222374 | A1 | 11/2004 | Scheidemann et al. | 250/299 |
| 2005/0017166 | A1 | 1/2005 | Scheidemann et al. | 250/288 |
| 2005/0119868 | A1 | 6/2005 | Scheidemann et al. | 702/196 |
| 2005/0248826 | A1 | 11/2005 | Tsarev | 359/285 |
| 2006/0076482 | A1 | 4/2006 | Hobbs et al. | |

FOREIGN PATENT DOCUMENTS

| | | |
|---|---|---|
| GB | 650 861 | 3/1951 |
| GB | 674 729 | 7/1952 |
| GB | 1 396 937 | 6/1975 |
| GB | 2 249 426 | 5/1992 |
| WO | WO 99/16103 | 4/1999 |
| WO | WO 99/17865 | 4/1999 |
| WO | WO 00/20851 | 4/2000 |

OTHER PUBLICATIONS

Charles Evans & Associates, Specialists in Materials Characterization, "Secondary Ion Detectors," URL=http://www.eaglabs.com/cai/simsinst/detector.htm, download date Mar. 3, 2005.

"Microchannel Plate Principals of Operation," URL=http://hea-www.harvard.edu/HRC/mcp/mcp.html, download date of Mar. 3, 2005.

Wiza, J., "Microchannel Plate Detectors," Reprinted from *Nuclear Instruments and Methods*, 162(1-3 part 2), Jun. 1, 1979, pp. 587-601.

U.S. Appl. No. 60/061,394, filed Oct. 7, 1997, Scheidemann et al.
U.S. Appl. No. 60/358,124, filed Feb. 20, 2002, Scheidemann et al.
U.S. Appl. No. 60/468,780, filed May 7, 2003, Scheidemann et al.
U.S. Appl. No. 60/484,801, filed Jul. 3, 2003, Scheidemann et al.
U.S. Appl. No. 60/497,799, filed Aug. 26, 2003, Scheidemann.
U.S. Appl. No. 60/506,521, filed Sep. 25, 2003, Scheidemann.
U.S. Appl. No. 60/550,663, filed Mar. 5, 2004, Scheidemann et al.
U.S. Appl. No. 60/550,664, filed Mar. 5, 2004, Scheidemann et al.
U.S. Appl. No. 60/557,920, filed Mar. 31, 2004, Scheidemann et al.
U.S. Appl. No. 60/557,968, filed Mar. 31, 2004, Scheidemann et al.
U.S. Appl. No. 60/557,969, filed Mar. 31, 2004, Scheidemann et al.
U.S. Appl. No. 60/601,803, filed Aug. 16, 2004, Scheidemann et al.
U.S. Appl. No. 60/601,810, filed Aug. 16, 2004, McGraw et al.
U.S. Appl. No. 60/601,867, filed Aug. 16, 2004, Long et al.

Bobeldijk et al., "Testing the Performance of a VUV Photoionization Source on a Double Focussing Mass Spectrometer using Alkanes and Thiophenes," *International Journal of Mass Spectrometry and Ion Processes* 110:179-194, Dec. 2, 1991.

Bramer et al., "Tunable, Coherent Vacuum Ultraviolet Radiation for Photoionization Mass Spectrometry," *Applied Spectroscopy* 46(2):255-261, Feb. 1992.

Brion, "A Windowless Photoionization Source for High Resolution Analytical Mass Spectrometers," *Analytical Chemistry* 37(13):1706-1709, Dec. 1965.

Burgoyne et al., "Design and Performance of a Plasma-Source Mass Spectrograph," *J. American Society of Mass Spectrometry* 8:307-318, 1997.

Darling et al., "Micromachined Faraday Cup Array Using Deep Reactive Ion Etching," *Sensors and Actuators A* 95:84-93, 2002.

Darling et al., "Micromachined Faraday Cup Array Using Deep Reactive Ion Etching," *IEEE*, pp. 90-93, 2001.

Dodson, "Stabilization of Magnetic Field using a Flux-Integrating Circuit," *Journal of Physics E: Scientific Instruments* 3:708-710, 1970.

Hadfield et al., "Permanent Magnets for Spectrographs and Nuclear Physical Research," *British Journal of Applied Physics* 3:199-202, Jun. 1952.

High Resolution Camera, "Microchannel Plate Principles of Operation," URL: http://hea-www.harvard.edu/HRC/mcp/mcp.html, accessed Feb. 2, 2005, 3 pages.

Nier et al., "High-performance Double-Focusing Mass Spectrometer," *Rev. Sci. Instrum.* 56 (2):214-219, Feb. 1985.

Scheidemann et al., "Faraday Cup Detector Array with Electronic Multiplexing for Multichannel Mass Spectrometry," *J. Vac. Sci. Technol. A* 20(3):597-604, May/Jun. 2002.

Van Bramer et al., "Tunable, Coherent Vacuum Ultraviolet Radiation for Photoionization Mass Spectrometry," *Applied Spectroscopy* 46(2):255-261, Feb. 1992.

Van Der Walt, "The Control and Stabilization of the Magnetic Field for a Mass Spectrometer," *The Review of Scientific Instruments* 24(6):413-416, Jun. 1953.

\* cited by examiner

FOCAL PLANE DETECTOR ASSEMBLY OF A MASS SPECTROMETER

CROSS-REFERENCE TO RELATED APPLICATION

This application claims the benefit of U.S. Provisional Patent Application No. 60/557,920, filed on Mar. 31, 2004; U.S. Provisional Patent Application No. 60/557,969, filed on Mar. 31, 2004; U.S. Provisional Patent Application No. 60/550,663, filed on Mar. 5, 2004; and U.S. Provisional Patent Application No. 60/550,664, filed on Mar. 5, 2004.

BACKGROUND OF THE INVENTION

1. Field of the Invention

The present invention disclosure is directed generally to the field of mass spectrometers, and in particular to focal plane detectors thereof.

2. Description of the Related Art

Mass spectrometry is widely used in many applications ranging from process monitoring to life sciences. Over the course of the last 60 years, a wide variety of instruments has been developed. The focus of new developments has been two fold: (1) a push for ever higher mass range with high mass resolution, and (2) on developing small, desktop mass spectrometry instruments.

Mass spectrometers are often coupled with gas chromatographs for analysis of complex mixtures. This is particularly useful for analysis of volatile organic compounds (VOCs) and semi-volatile organic compounds (semi-VOCs). A combined gas chromatograph and mass spectrometer or spectrograph (GC/MS) instrument typically includes a gas inlet system, which may include the gas chromatograph portion of the GC/MS instrument. The GC/MS instrument typically also includes an electron impact (EI) based ionizer with ion extractor, ion optic components to focus the ion beam, ion separation components, and ion detection components. Ionization can also be carried out via chemical ionization.

Ion separation can be performed in the time or spatial domain. An example for mass separation in the time domain is a time of flight mass spectrometer. Spatial separation is seen in commonly used quadrupole mass spectrometers. Here the "quadrupole filter" allows only one mass/charge ratio to be transmitted from the ionizer to the detector. A full mass spectrum is recorded by scanning the mass range through the "mass filter." Other spatial separation is based on magnetic fields where either the ion energy or the magnetic field strength is varied, again the mass filter allowing only one mass/charge ratio to be transmitted and a spectrum can be recorded by scanning through the mass range.

One type of mass spectrometer is a mass spectrograph. In a mass spectrograph the ions are spatially separated in a magnetic field and detected with a position sensitive detector. The concept of a double focusing mass spectrograph was first introduced by Mattauch and Herzog (MH) in 1940 (J. Mattauch, Ergebnisse der exakten Naturwissenschaften, vol. 19, pages 170-236, 1940).

Double focusing refers to an instrument's ability to refocus both the energy spread as well as the spatial beam spread. Modern developments in magnet and micro machining technologies allow dramatic reductions in the size of these instruments. The length of the focal plane in a mass spectrometer capable of VOC and semi-VOC analysis is reduced to a few centimeters.

The typical specifications of a small confocal plane layout Mattauch-Herzog instrument are summarized below:

Electron impact ionization, Rhenium filament
DC-voltages and permanent magnet
Ion Energy: 0.5-2.5 kV DC
Mass Range: 2-200 D
Faraday cup detector array or strip charge detector
Integrating operational amplifier with up to $10^{11}$ gain
Duty Cycle: >99%
Read-Out time: 0.03 sec to 10 sec
Sensitivity: approximately 10 ppm with strip charge detector In addition, the ion optic elements are mounted in the vacuum chamber floor or on chamber walls. The optics can also be an integral part of the vacuum housing. In small instruments, however, the ion optic elements can be built on a base plate which acts as an "optical bench." This bench supports the ion optic elements. The base plate is mounted against a vacuum or master flange to provide a vacuum seal needed to operate the mass spectrometer under vacuum. The base plate can also function as the vacuum or master flange itself.

A Mattauch-Herzog ion detector is a position sensitive detector. Numerous concepts have been developed over the last decades. Recent developments focus on solid state based direct ion detection as an alternative to previously used electro optical ion detection (EOID).

The electro optical ion detector (EOID) converts the ions in a multi-channel-plate (MCP) into electrons, amplifies the electrons (in the same MCP), and illuminates a phosphorus film bombarded with the electrons emitted from the MCP. The image formed on phosphorus film is recorded with a photo diode array via a fiber optic coupler. This type of EOID is described in detail in U.S. Pat. No. 5,801,380. The EOID is intended for the simultaneous measurement of ions spatially separated along the focal plane of the mass spectrometer. The EOID operates by converting ions to electrons and then to photons. The photons form images of the ion-induced signals. The ions generate electrons by impinging on a microchannel electron multiplier array. The electrons are accelerated to a phosphor-coated fiber-optic plate that generates photon images. These images are detected using a photodetector array.

According to a different configuration, a direct charge measurement can be based on a micro-machined Faraday cup detector array. Here, an array of individually addressable Faraday cups monitors the ion beam. The charge collected in individual elements of the array is handed over to an amplifier via a multiplexer unit. This layout reduces the number of amplifiers and feedthroughs needed. This concept is described in detail in recent publications, such as "A. A. Scheidemann, R. B. Darling, F. J. Schumacher, and A. Isakarov, Tech. Digest of the 14th Int. Forum on Process Analytical Chem. (IFPAC-2000), Lake Las Vegas, Nev., Jan. 23-26, 2000, abstract 1-067"; "R. B. Darling, A. A. Scheidemann, K. N. Bhat, and T.-C. Chen., Proc. of the 14th IEEE Int. Conf. on Micro Electro Mechanical Systems (MEMS-2001), Interlaken, Switzerland, Jan. 21-25, 2001, pp. 90-93"; and Non-Provisional patent application Ser. No. 09/744,360 titled "Charged Particle Beam Detection System."

Other important references regarding spectrometers are Nier, D. J. Schlutter Rev. Sci. Instrum. 56(2), page 214-219, 1985; "Fundamentals of Focal Plane Detector cs" K. Birkinshaw Jrnl. of Mass Spectrometry, Vol. 32,795-806 (1997); and T. W. Burgoyne et. al. J. Am. Soc. Mass Spectrum 8, pages 307-318, 1997.

Alternatively, especially for low energy ions, a flat metallic strip (referred to as a strip charge detector (SCD)) on a grounded and insulated background can be used with an MCP. As described above, an MCP converts ions into electrons and amplifies the electrons. The SCD detects the electrons and generates a charge. Again the charge is handed over to an amplifier via a multiplexer.

Another embodiment of an ion detector array is disclosed in U.S. Pat. No. 6,576,899 and is referred to as a shift register based direct ion detector.

The shift register based direct ion detector defines a charge sensing system that can be used in a GC/MS system, with a modification to allow direct measurement of ions in the mass spectrometer device without conversion to electrons and photons (e.g., EOID prior to measurement). The detector may use charge coupled device (CCD) technology with metal oxide semiconductors. The GC/MS system may use direct detection and collection of the charged particles using the detector. The detected charged particles form the equivalent of an image charge that directly accumulates in a shift register associated with a part of the CCD. This signal charge can be clocked through the CCD in a conventional way, to a single output amplifier. Since the CCD uses only one charge-to-voltage conversion amplifier for the entire detector, signal gains and offset variation of individual elements in the detector array are minimized.

A Mattauch-Herzog detector array, which can be composed of a Faraday cup detector array, a strip charge detector, or another type of the aforementioned detectors, is placed at the exit end of the magnet, which is commonly designed to be coplanar with the focal plane of the device.

The Faraday cup detector array (FCDA) can be made by deep reactive ion etching (DRIE). The strip charge detector (SCD) can be made by vapor deposition. A die with an active element (FCDA or SCD) is usually cut out of a wafer with conventional techniques such as laser cutting or sawing.

The FCDA or SCD die is placed in front of the magnet and electronically connected to the multiplexer and amplifier unit, which is referred to as a "FARADAY CUP DETECTOR ARRAY"—"INPUT/OUTPUT"—"PRINTED CIRCUIT BOAR" (FCDA-I/O-PCB), to read out the charge collected with the detector elements.

Patents representing major advances in the art of mass spectrometers and gas chromatographs/mass spectrometers are U.S. Pat. Nos. 5,317,151; 5,801,380; 6,046,451; 6,182,831; 6,191,419; 6,403,956; 6,576,899; and 6,847,036. Also U.S. patent application Ser. Nos. 10/811,576 and 10/860,776.

BRIEF SUMMARY OF THE INVENTION

In one aspect, a focal plane detector assembly of a mass spectrometer comprises an ion detector configured to detect ions crossing a focal plane of the spectrometer and an electrically conductive mesh lying in a plane parallel to the focal plane and positioned such that ions exiting a magnet of the mass spectrometer pass through the mesh before contacting the ion detector. The mesh is maintained at a low voltage potential, relative to a circuit ground. The mesh may be mounted directly to the magnet or positioned some distance away.

The ion detector includes a microchannel plate electron multiplier and a detector array positioned and configured to detect electrons emitting from a the first microchannel plate electron multiplier. Ions transiting the magnet are shielded by the mesh from a high negative voltage field generated by a negative potential on a first face of the electron multiplier.

According to another embodiment of the invention, the first face of the electron multiplier is maintained at a much lower voltage level, i.e., much closer to circuit ground, thus avoiding the formation of a negative field, and obviating the need for the mesh.

The detector array may include any suitable device, such as a faraday cup detector array, a strip charge detector array, or a CCD detector array.

BRIEF DESCRIPTION OF THE SEVERAL VIEWS OF THE DRAWING(S)

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE INVENTION

In the following description, certain specific details are set forth in order to provide a thorough understanding of various embodiments of the invention. However, one skilled in the art will understand that an embodiment may be practiced without these details. In other instances, well-known structures associated with a mass spectrometer, such as computers, microprocessors, memories, and the like have not been shown or described in detail to avoid unnecessarily obscuring descriptions of the illustrated embodiments.

Unless the context requires otherwise, throughout the specification and claims which follow, the word "comprise" and variations thereof, such as, "comprises" and "comprising" are to be construed in an open, inclusive sense, that is as "including, but not limited to."

Figure 1:
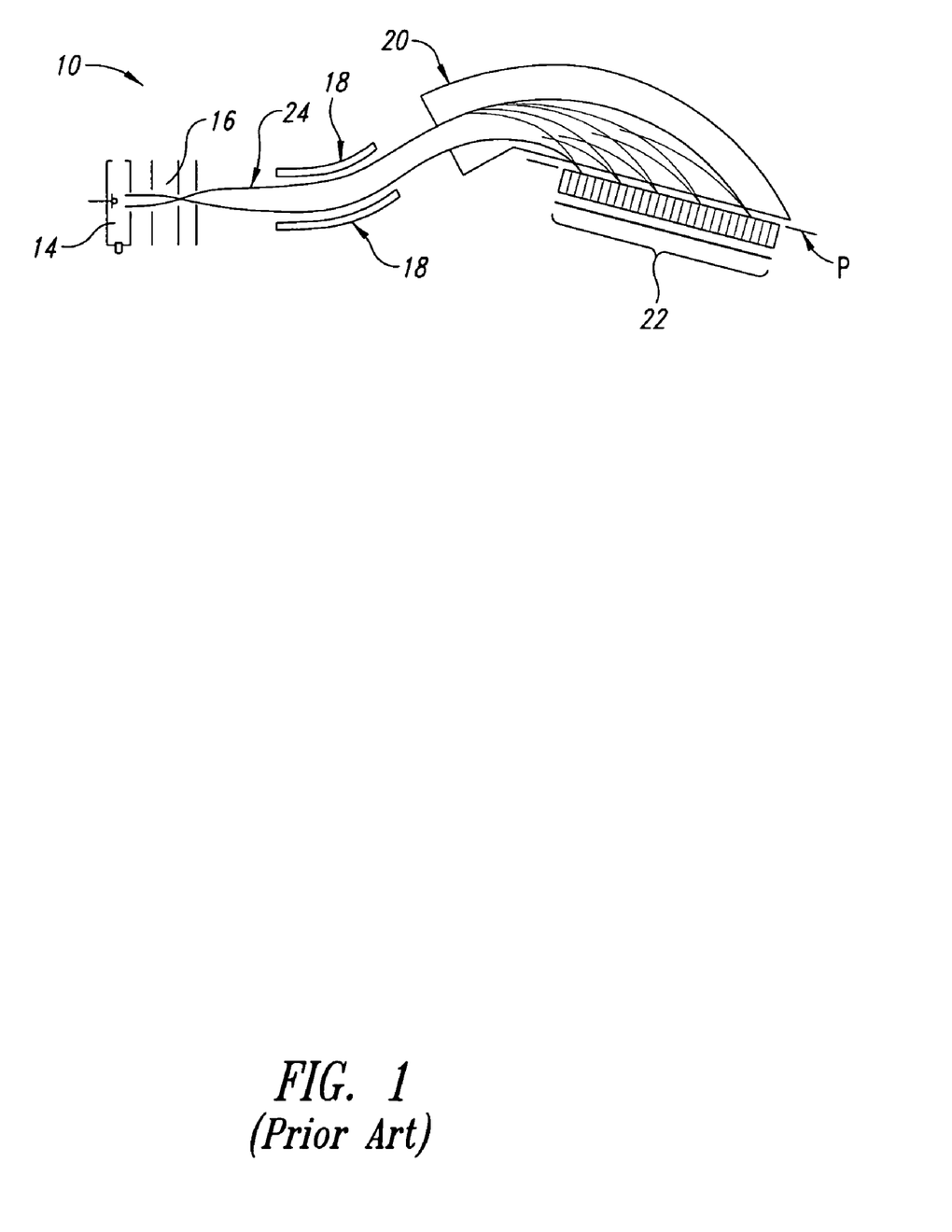
FIG. 1 is a diagrammatic representation of a dual focus mass spectrometer according to known art.

FIG. 1 shows a conventional double focus mass spectrometer 10. The mass spectrometer 10 comprises an ionizer 14, a shunt and aperture 16, an electrostatic energy analyzer 18, a magnet 20, and a focal plane section 22.

In operation, gaseous or vaporized material is introduced into the ionizer 14, where it is bombarded by electrons, thus producing ions, which are focused by the shunt and aperture section 16 to produce an ion beam 24. Paths of the ions are adjusted according to their electrical charge by the electrostatic energy analyzer 18, and separated according to their charge/mass ratio in the magnet 20. The ions exiting magnet 20 are separated and distributed spatially according to their charge/mass ratios, their electrical characteristics having been compensated for by the electrostatic energy analyzer 18. The physics of the energy analyzer 18 and the magnet 20 are selected such that ions of any charge mass ratio within a selected range of ratios reach a point of maximum resolution in a common plane P. This plane P is referred to as the focal plane of the mass spectrometer.

As described in more detail in the background section of this specification, the focal plane section 22 includes sensors, amplifiers, and processors configured to detect and record the position of ions crossing the focal plane P as well as the relative quantities of ions crossing the plane P at any given point thereon. Accordingly, it is desirable that the sensors of the focal plane section 22 be sensitive to individual ions crossing the focal plane P, as well as large masses of ions crossing at a common point on the plane P. Additionally, resolution is important to enable the differentiation between ions having different, but very similar, mass charge ratios.

Figure 2:
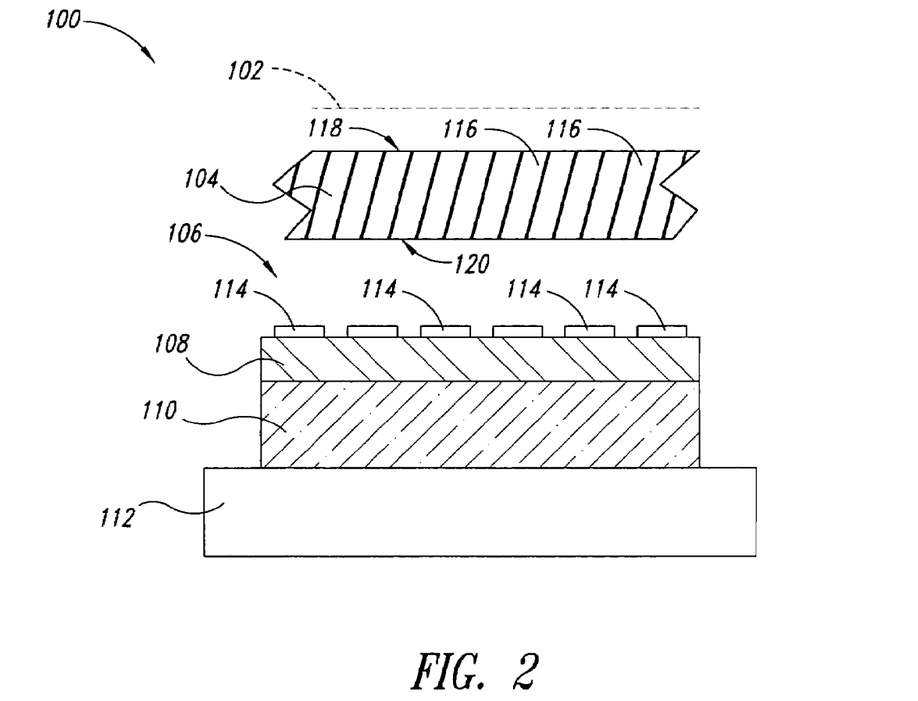
FIG. 2 is a schematic diagram of a focal plane detector according to one illustrated embodiment.

Referring to FIG. 2, a focal plane detector assembly 100 is shown, according to one illustrated embodiment. The detector assembly 100 includes a conductive mesh 102, a microchannel plate (MCP) 104, a strip charge detector array (SCD) 106, an insulator 108, a silicon substrate 110, and an assembly mount 112. The detector assembly 100 is configured to be positioned such that the mesh 102 is coplanar with the focal plane P of a mass spectrometer such as that pictured in FIG. 1.

The SCD 106 and the insulator 108 are formed using known semiconductor manufacturing techniques on the semiconductor substrate 110. The SCD 106 comprises a plurality of detector electrodes 114 coupled to logic circuitry, processors, memories, etc.

The microchannel plate 104 includes a plurality of capillary tubes 116 passing from a first face 118 to a second face 120. The second face 120 may be opposite the first face 118, as illustrated in FIG. 2. The first and second faces 118, 120 of the MCP 104 each include a conductive layer configured to receive an electrical charge.

The term "first face" is used in this specification generally to refer a face or side of a device facing into an oncoming stream of ions, and "second face" is used to refer to a face or side opposing the first face.

In operation, the first face 118 of the MCP 104 is maintained at a negative voltage potential relative to the second face 120. For example, the first face 118 may have a voltage potential of −1400 volts, while the second face 120 has a voltage potential of −500 volts, resulting in a voltage differential of 900 volts, from the first face 118 to the second face 120. When an ion strikes the first face 118 of the MCP 104, it enters one of the tubes 116 and impacts a sidewall of the tube 116. The impact of the ion causes a number of electrons to be ejected from the sidewall.

Because of the positive charge of the second face 120, relative to the first face 118, the electrons ejected from the sidewall of the tube 116 are drawn toward the second face 120. As the electrons move down the tube 116, the electrons, in turn, each strike the sidewall, causing additional electrons to be ejected therefrom. This process continues until a cloud of electrons exits the tube 116 at the second face of the MCP 104. The electrons exiting the tube 116 disburse into a space between the MCP 104 and the strip charge detector array 106. Electrons striking the electrodes 114 of the strip charge detector array 106 induce a current in the respective electrode 114, which is detected by the detection circuitry. Inasmuch as electrons disburse outward from the second face 120 of the MCP 104 in all directions, it is desirable that the space between the second face 120 of the MCP 104 and the strip charge detector array 106 be maintained as close together as possible to maintain resolution.

According to one embodiment, the MCP 104 has a voltage differential of greater than 500 volts, from the first face 118 to the second face 120.

Referring again to FIG. 1, it may be seen that the stream of ions 24 enters the magnet 20 at a sharp angle with respect to the focal plane P. The process of ionizing a sample in the ionizer 14 involves removing one or more electrons from the molecules of the sample. Accordingly, the ions in the ion beam 24 are positively charged. As the ions enter the magnet 20, the magnetic force bends the path of the individual ions according to their respective mass/weight ratios. However, the high negative voltage at the first face 118 of the MCP 104 creates an electrical field that is attractive to the positively charged ions in the magnet 20. Thus, the paths of the ions can be undesirably distorted by the negative charge on the surface of the MCP 104.

When the detector assembly 100 is properly positioned at the focal plane P, the mesh 102 is positioned between the MCP 104 and a back face of the magnet 20, and is provided with a low voltage potential. For example, the mesh 102 may be electrically coupled to circuit ground, or may be maintained at a voltage of less than 100 volts. The mesh 102 serves to block the strong negative electrical field of the MCP 104, preventing that electrical field from influencing the paths of the ions as they approach the focal plane P. The effectiveness of the mesh 102 at blocking the electrical field is inversely related to the size of the openings in the mesh 102. On the other hand, ions that actually contact the material of the mesh will not pass through to make contact with the MCP, so it is desirable that the mesh 102 be substantially transparent to the ions. Given these constraints, a very fine mesh 102 having an open area exceeding 80% or 90% is preferable. The mesh 102 may have a thickness of less than 0.5 millimeters.

Figure 3:
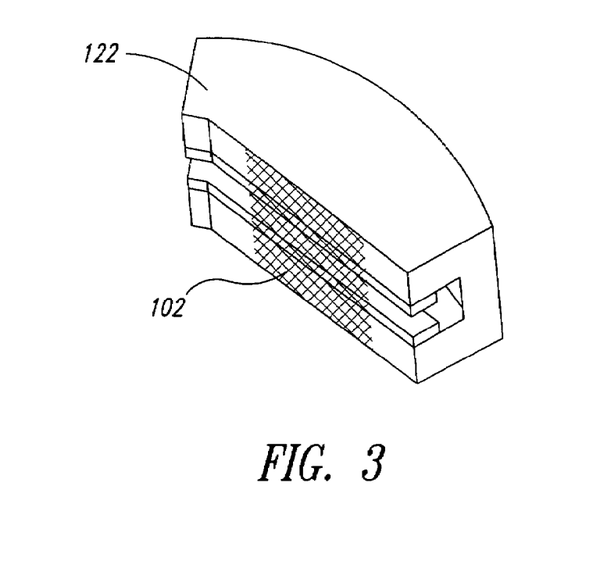
FIG. 3 is an isometric view of a magnet of a mass spectrometer with a mesh positioned thereon according to one illustrated embodiment.

Referring now to FIG. 3, a magnet 122, similar to the magnet 20 shown in FIG. 1, is provided with a mesh 102 affixed thereto. In the embodiment of FIG. 3, the mesh 102 and the magnet 122 are maintained at ground potential. In other embodiments, the mesh 102 may be separate from the magnet 122, and maintained at a different voltage potential, although it is preferable that a voltage difference between the mesh 102 and the magnet 122 be minimal. For example, according to an embodiment, the mesh 102 is maintained at less than 500 volts relative to a potential of the magnet 122. According to another embodiment, the mesh 102 is maintained at less than 100 volts, absolute.

The term "absolute" is used in this specification to refer to a voltage potential, without reference to polarity.

Figure 4:
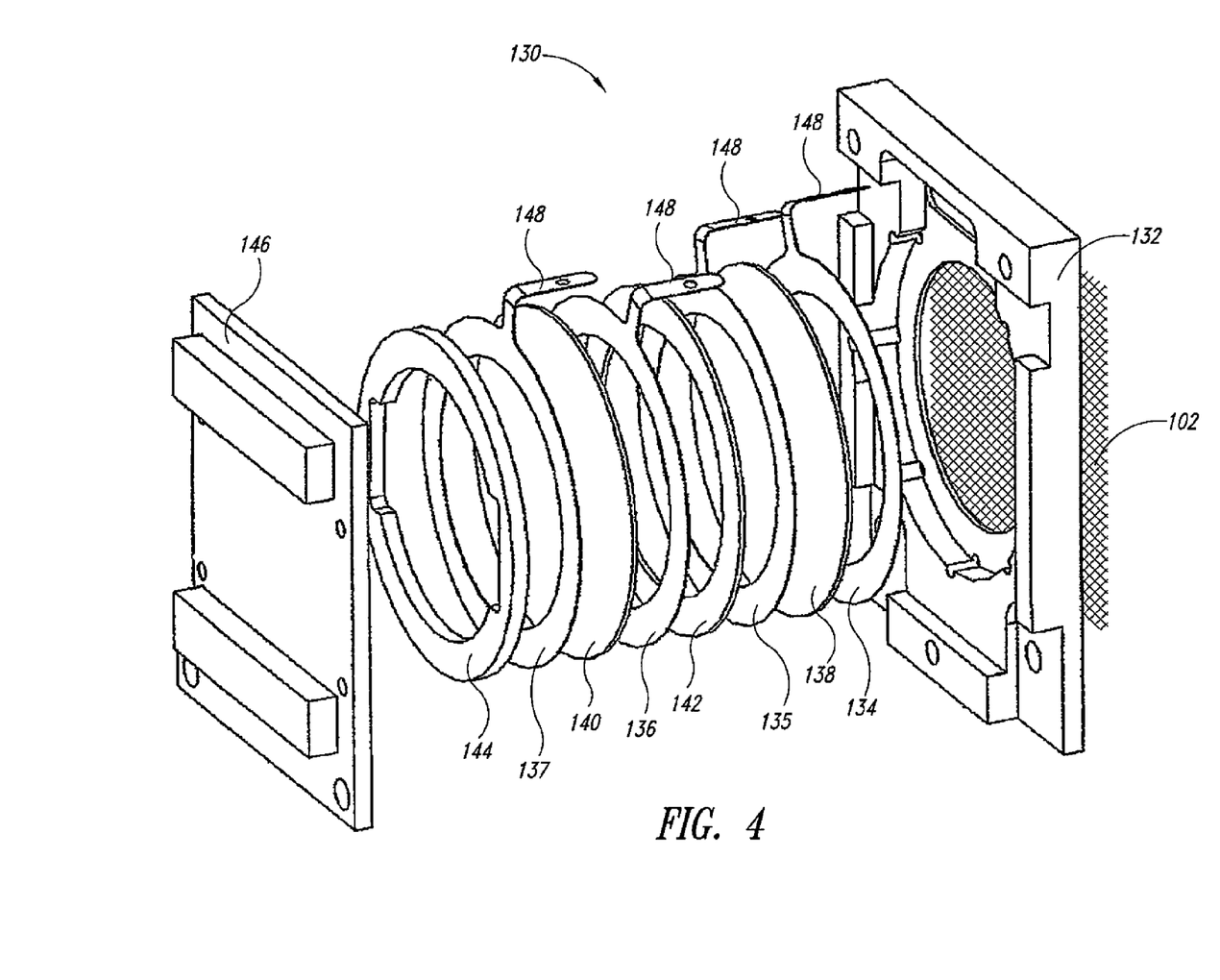
FIG. 4 is an exploded isometric view of a focal plane detector array according to another illustrated embodiment.
Figure 5:
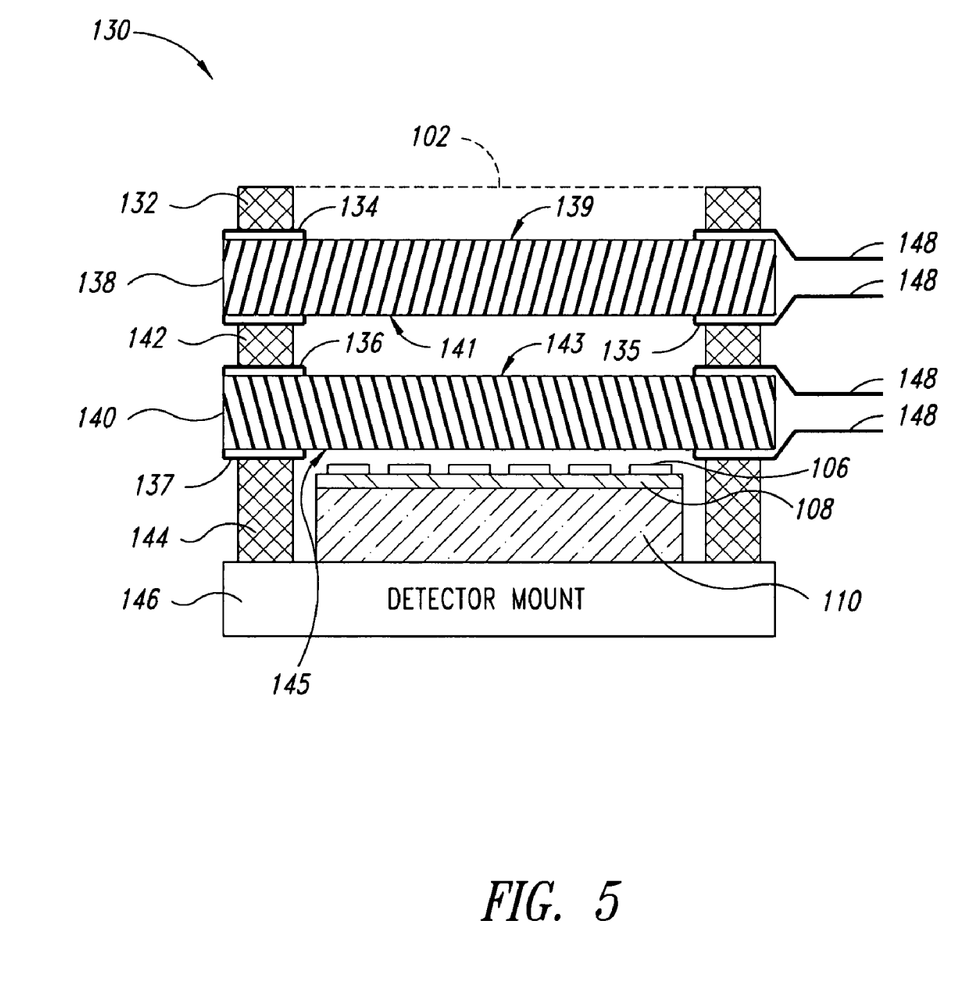
FIG. 5 is a schematic diagram of the focal plane detector of FIG. 4.

Turning now to FIGS. 4 and 5, a focal plane detector assembly 130 is shown according to another illustrated embodiment. The detector assembly 130 comprises first, second, third, and fourth electrodes 134-137, first and second MCPs 138, 140, insulating spacers 142, 144, detector mount 146, and assembly holder 132.

The assembly 130 is shown diagrammatically in FIG. 5. The assembly 130 is configured to be attached to a base support by the assembly holder 132. Fasteners (not shown) bias the detector mount 146 to the assembly holder 132, sandwiching the other components thereof between. As described previously with reference to MCP 104 of FIG. 2, an MCP amplifies an electron cascade. In the case of the assembly 130, the first MCP 138 is configured to receive ions passing through the focal plane and produce a cascade of electrons in response. The second MCP 140 receives the electrons from the first MCP 138 and amplifies the cascade of ions to provide a stronger signal to the strip charge detector array 106. The first, second, third, and fourth electrodes 134-137 are each provided with voltage charges via terminals 148 to energize first and second faces of the respective MCP. First and second insulating spacers 142, 144 are provided to electrically isolate components of the assembly 130. The assembly holder 132 may also be nonconductive to insulate the detector assembly 130 from the mesh 102 and other components a the spectrometer in which it is employed, or may include a separate insulator.

According to an embodiment, a voltage difference across the first to second faces of each of the MCPs 138, 140 is in the range of around 500-900 volts, and is provided at the respective electrodes 134-137. Additionally, a voltage difference between the second electrode 135 and the third electrode 136 may be equal to or greater tha zero.

Components of the assembly may be spaced as closely as possible together without making electrical contact In order to maximize resolution of the assembly. For example, according to one embodiment, the mesh 102 is be placed directly at the focal plane P, or within 1 millimeter thereof. A first face 139 of the first MCP 138 may be positioned within 2 millimeters of the mesh 102, and preferably within 0.5 millimeters. According to an embodiment of the invention, a first face 143 of the second MCP 140 is positioned within 2 millimeters of a second face 141 of the first MCP 138, and preferably within 0.5 millimeters.

According to one embodiment, the first face 139 of the first MCP 138 is maintained at a relatively low voltage level, such that an electrical field created thereby does not have sufficient strength to interfere with the operation of the magnet 122. For example, the first face 139 of the first MCP 138 may have a potential of less than 100 volts, absolute. Voltage levels of other components of the assembly are selected to maintain desired voltage differences as outlined above. In accordance with this embodiment, the mesh 102 is not required, since there is no appreciable electrical field.

Figure 6:
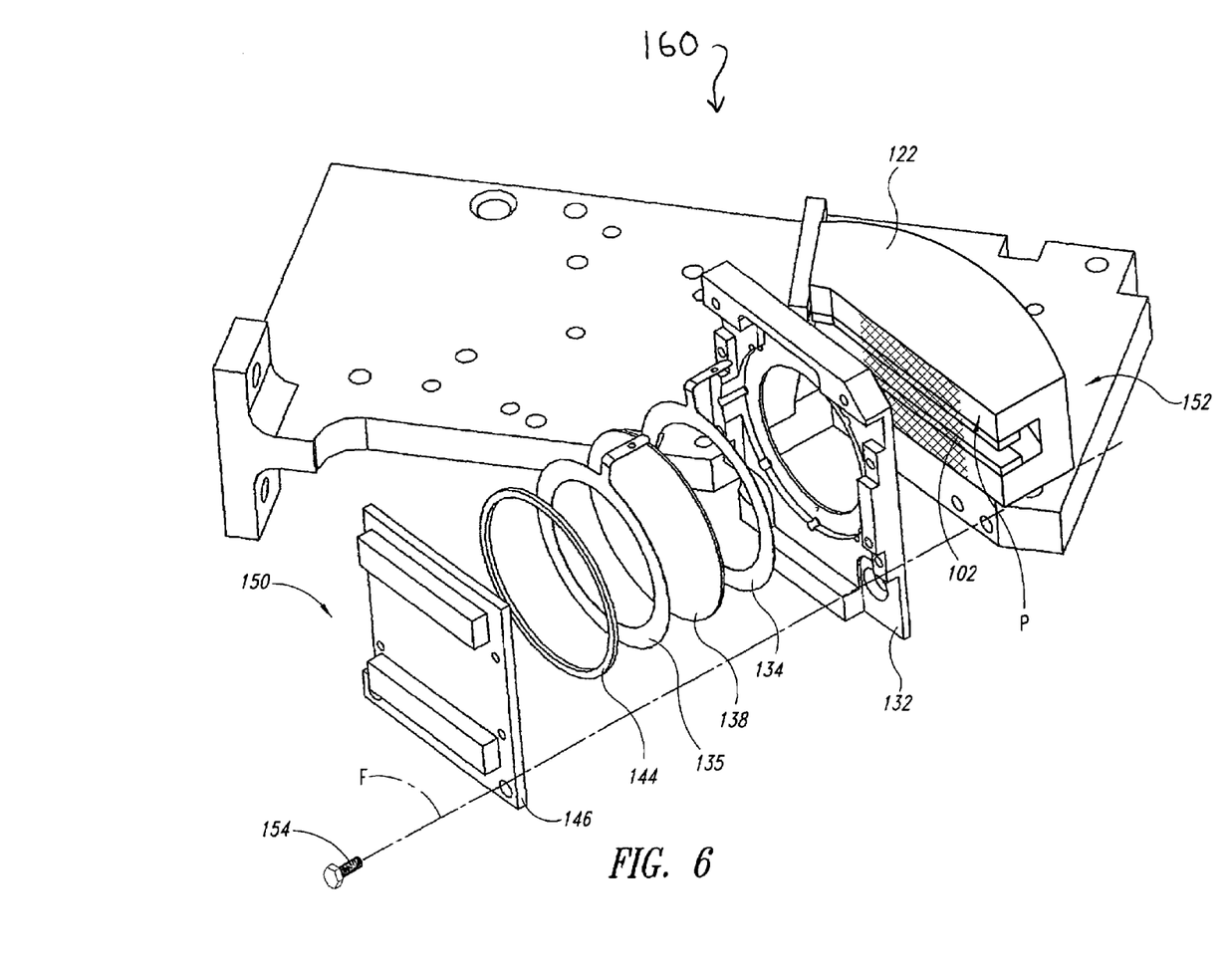
FIG. 6 is a partially exploded isometric view of a focal plane detector array according to an additional illustrated embodiment.

Turning now to FIG. 6, another embodiment is shown. In this embodiment, a focal plane detector assembly 150 is provided. A primary difference between the assembly 150 of FIG. 6 and the assembly 130 of FIGS. 4 and 5 is that assembly 150 is shown as having only a single MCP 138. In other respects, assemblies 150 and 130 are quite similar. FIG. 6 also shows a base plate 152 configured to receive various components of a mass spectrometer 160. The magnet 122 is shown positioned on the base plate 152 and the mesh 102 is shown positioned at the focal plane P of the spectrometer 160. A fastener 154 is shown in position to fasten the detector mount 146 and the assembly holder 132 to the base plate 152 along the line F. It will be recognized that the assembly 130 of FIGS. 4 and 5 is similarly configured to be attached to a base plate in a similar manner.

In the device shown in FIG. 6, the focal plane P is coplanar with the face of the magnet 122. In other embodiments, the focal plane P may be separated from the magnet 122 by some distance. For example, according to an embodiment, a spectrometer system is configured such that the focal plane is spaced away from a back face of the magnet, the mesh 102 is between the focal plane and the back face of the magnet, and separated a small distance from the first face of an MCP, while the first face of the MCP is positioned precisely at the focal plane.

While the mesh 102 is described as being attached to a back face of the magnet 122, according to another embodiment, the mesh 102 is attached to the assembly holder 132 such that the assembly holder 132 forms an insulator between the mesh and the first electrode 134. According to an alternate embodiment, the mesh 102 is positioned between the assembly holder 132 and the first electrode 134, in which case another insulator is provided between the mesh 102 and the first electrode 134.

The invention has been described with reference to a double focus mass spectrometer and with reference to a strip charge detector array. These embodiments are described for illustration only, and do not limit the scope of the invention. For example, the detector array may include a Faraday cup detector array or a CCD type detector array. According to an embodiment of the invention, the detector assembly may include a direct charge measuring device.

All of the above U.S. patents, U.S. patent application publications, U.S. patent applications, foreign patents, foreign patent applications and non-patent publications referred to in this specification and/or listed in the Application Data Sheet including but not limited to U.S. Provisional Patent Application No. 60/557,920; U.S. Provisional Patent Application No. 60/557,969; U.S. Provisional Patent Application No. 60/550,663; and U.S. Provisional Patent Application No. 60/550,664; U.S. Non-Provisional Patent Application 10/811,576; U.S. Non-Provisional Patent Application 10/860,776; U.S. Pat. No. 5,317,151; U.S. Pat. No. 5,801,380; U.S. Pat. No. 6,046,451; U.S. Pat. No. 6,182,831; U.S. Pat. No. 6,191,419; U.S. Pat. No. 6,403,956; U.S. Pat. No. 6,576,899; and U.S. Pat. No. 6,847,036, are incorporated herein by reference, in their entirety.

In addition, the published materials by J. Mattauch, Ergebnisse der exakten Naturwissenschaften, vol. 19, pages 170-236, 1940; "Fundamentals of Focal Plane Detector cs" K. Birkinshaw Jrnl. of Mass Spectrometry, Vol. 32,795-806 (1997); A. A. Scheidemann, R. B. Darling, F. J. Schumacher, and A. Isakarov, Tech. Digest of the 14th Int. Forum on Process Analytical Chem. (IFPAC-2000), Lake Las Vegas, Nev., Jan. 23-26, 2000, abstract 1-067"; "R. B. Darling, A. A. Scheidemann, K. N. Bhat, and T.-C. Chen., Proc. of the 14th IEEE Int. Conf. on Micro Electro Mechanical Systems (MEMS-2001), Interlaken, Switzerland, Jan. 21-25, 2001, pp. 90-93; Nier, D. J. Schlutter Rev. Sci. Instrum. 56(2), page 214-219, 1985; and T. W. Burgoyne et. al., J. Am. Soc. Mass Spectrum 8, pages 307-318, 1997, are incorporated by reference in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A focal plane detector assembly of a mass spectrometer, comprising:
    an ion detector having a first face lying in a first plane parallel to the focal plane of the mass spectrometer and including:
        a first microchannel plate electron multiplier, a first face thereof defining the first face of the ion detector, and
        a CCD detector array positioned and configured to detect electrons emitting from a second face of the first microchannel plate electron multiplier; and
    an electrically conductive mesh lying in a second plane parallel to the focal plane of the mass spectrometer and having a first voltage potential, the mesh being positioned such that ions exiting a magnet of the mass spectrometer pass through the mesh before contacting the ion detector.

2. The assembly of claim 1 wherein the second plane is coplanar with the focal plane.

3. The assembly of claim 1 wherein the second plane is separated from the focal plane by less than 1 millimeters.

4. The assembly of claim 1 wherein the first and second planes are separated by less than 2 millimeters.

5. The assembly of claim 1 wherein the mesh has a transparency to ions of greater than 80%.

6. The assembly of claim 1 wherein the mesh is mounted on a face of the magnet, and is electrically continuous therewith.

7. The assembly of claim 1 wherein the first voltage potential is approximately equal to or less than about 100 volts, absolute.

8. The assembly of claim 1 wherein a face of the magnet has a second voltage potential.

9. The assembly of claim 8 wherein a difference between the first and second voltage potentials is less than 500 volts.

10. The assembly of claim 1 wherein the first face of the first microchannel plate electron multiplier has a negative voltage potential relative to the first voltage potential.

11. The assembly of claim 10 wherein the first face of the microchannel plate electron multiplier has a negative voltage potential relative to a second face thereof.

12. The assembly of claim 10 wherein the first face of the microchannel plate electron multiplier has a voltage potential of greater than −500 volts relative to a second face thereof.

13. The assembly of claim 1 wherein the ion detector comprises:
at least a second microchannel plate electron multiplier positioned between the first microchannel plate electron multiplier and the CCD detector array.

14. The assembly of claim 13 wherein the first and second microchannel plate electron multipliers are separated by an insulator.

15. The assembly of claim 13 wherein a second face of the first microchannel plate electron multiplier and a first face of the second microchannel plate electron multiplier are separated by less than 2 millimeters.

16. The assembly of claim 13 wherein a second face of the first microchannel plate electron multiplier and a first face of the second microchannel plate electron multiplier are separated by less than 0.5 millimeters.

17. The assembly of claim 1 wherein the ion detector comprises:
an assembly holder to which the first microchannel plate electron multiplier and the detector array are coupled.

18. The assembly of claim 17 wherein the mesh is coupled to the assembly holder.

19. A focal plane detector assembly of a mass spectrometer, comprising:
a first microchannel plate electron multiplier, a first face thereof lying in a first plane parallel to the focal plane of the mass spectrometer and facing a magnet of the mass spectrometer, the first face having a voltage difference of less than 100 volts, relative to the magnet; and
a CCD detector array positioned and configured to detect electrons emitting from a second face of the first microchannel plate electron multiplier.

20. The assembly of claim 19, further comprising:
at least a second microchannel plate electron multiplier positioned between the first microchannel plate electron multiplier and the detector array.

21. A mass spectrometer, comprising:
an ion source configured to emit ions in a focused stream;
a focal plane detector configured to receive at least a portion of the ions of the ion stream, and including a microchannel plate electron multiplier and a CCD detector array positioned to detect electrons emitting from the microchannel plate electron multiplier; and
shielding means for shielding the ions of the stream from a voltage potential at the focal plane detector until the ions reach a focal plane of the spectrometer.

22. The mass spectrometer of claim 21 wherein the shielding means comprises an electrically conductive mesh lying in a plane parallel to the focal plane of the mass spectrometer.

23. The mass spectrometer of claim 22 wherein the mesh has a voltage potential of less than 100 volts relative to a circuit ground of the mass spectrometer.

24. The mass spectrometer of claim 21 wherein a first face of the microchannel plate electron multiplier lies in a plane parallel to the focal plane of the mass spectrometer.

25. The mass spectrometer of claim 24 wherein the shielding means comprises the first face of the microchannel plate electron multiplier, the first face having a voltage potential of less than 100 volts relative to a circuit ground of the mass spectrometer.

26. A method, comprising:
generating a beam of ions;
deflecting ions of the beam according to a charge/mass ratio of the respective ions;
generating an electrical field in a microchannel plate electron multiplier capable of affecting ions of the beam;
shielding the ions of the beam from the electrical field until the ions of the beam pass an electrically conductive mesh;
receiving the ions of the beam into the microchannel plate electron multiplier; and
detecting electrons exiting the microchannel plate electron multiplier with a CCD detector array.

27. The method of claim 26 wherein the shielding step includes imparting a low voltage charge to the mesh interposed between ions being shielded and the microchannel plate electron multiplier.

28. The method of claim 26 wherein the low voltage charge is equal to a circuit ground.

29. The assembly of claim 19, further comprising:
an electrically conductive mesh lying in a second plane parallel to the focal plane of the mass spectrometer and between the first plane and the magnet of the mass spectrometer.

30. A mass spectrometer, comprising:
an ion source configured to emit ions in a focused stream;
a microchannel plate electron multiplier configured to receive at least a portion of the ions of the ion stream; and
a CCD detector array positioned to detect electrons emitting from the microchannel plate electron multiplier.

* * * * *